US00PP23683P2

(12) United States Plant Patent
Kordes

(10) Patent No.: US PP23,683 P2
(45) Date of Patent: Jun. 25, 2013

(54) FLORIBUNDA ROSE PLANT NAMED 'KORFLOCI67'

(50) Latin Name: *Rosa hybrida*
Varietal Denomination: KORfloci67

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 6 days.

(21) Appl. No.: 13/200,269

(22) Filed: Sep. 21, 2011

(51) Int. Cl.
*A01H 5/00* (2006.01)

(52) U.S. Cl.
USPC ..... Plt./141

(58) Field of Classification Search
USPC ..... Plt./141, 149, 123
See application file for complete search history.

*Primary Examiner* — Howard Locker

(57) ABSTRACT

A new and distinct variety of rose with long lasting, novel lavender flowers, and attractive foliage with good disease resistance. It exhibits vigorous growth and an upright to bushy habit with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida*.

Variety denomination: The denomination of the new variety is 'KORfloci67'.

CROSS REFERENCES AND FEDERAL R&D STATEMENT

There are no cross referenced or related applications. This variety was developed without the aid of any research grant.

The new variety of rose plant of the present invention originated from a controlled crossing in a breeding program of two distinct parents during the summer of 2004. The crossing was between an 'un-named seedling' and an 'un named-seedling'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORfloci67'.

SUMMARY OF THE INVENTION

The new rose plant may be distinguished from its seed parent, an 'un-named seedling' by the following combination of characteristics:

1. The flower color of 'KORfloci67' is lavender while the flower color of the seed parent is medium pink.
2. The flower size of 'KORfloci67' is small while the flower size of the seed parent is medium.

The new rose plant may be distinguished from its pollen parent, an 'un-named seedling' by the following combination of characteristics:

1. The growth habit of 'KORfloci67' is vigorous while the growth habit of the pollen parent is slow.
2. The disease resistance of 'KORfloci67' is good while the disease resistance of the pollen parent is low.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORfloci67' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORfloci67' was selected in May, 2005 from the seedling beds to be asexually propagated for further evaluation. The first asexual propagation of 'KORfloci67' was done by budding to seedling understocks in July, 2005 at the inventor's nursery in Offenseth-Sparrieshoop, Germany.

This initial and other subsequent propagations conducted in controlled environments demonstrate that 'KORfloci67' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORfloci67'.

DETAILED BOTANICAL DESCRIPTION

The following is a description of 'KORfloci67', as observed growing in July, 2011 in a nursery in Jackson County, Oreg. on plants of 2 years of age. Color references are made using The Royal Horticultural Society (London, England) Colour Chart, 2001 except where common terms of color are used.

For a comparison, several physical characteristics of the rose variety 'KORpot022', a rose variety from the same inventor described and illustrated in U.S. Plant Pat. No. 22,811 and filed on Apr. 14, 2011 are compared to 'KORfloci67' in Chart 1.

CHART 1

| Characteristic | 'KORfloci67' | 'KORpot022' |
|---|---|---|
| Average receptacle size: | 10 mm (h) × 8 mm (w). | 7 mm (h) × 4 mm (w). |
| Flower size: | Average flower diameter is 60 mm when open. | Average flower diameter is 45 mm when open. |
| Average plant height: | 70 cm (h) × 50 cm (w). | 20 cm (h) × 18 cm (w). |

Parents:

*Seed parent*.—An 'un-named seedling'.

*Pollen parent*.—An 'un-named seedling'.

Classification:

*Botanical classification*.—*Rosa hybrida* 'KORfloci67'.

*Commercial classification*.—Floribunda rose.

FLOWER AND FLOWER BUD

Blooming habit: Continuous.

Flower bud:

*Size*.—Upon opening, 22 mm in length from base of receptacle to distal end of bud and 10 mm diameter at its widest point.

*Bud form*.—Short. Pointed ovoid.

*Bud color*.—As sepals first unfold, bud color is Red-Purple Group N74C. When ¼ open, the upper surface of petals is Purple Group 77A and 77B, and the lower surface is Red-Purple Group 70B.

*Sepals*.—Color: Upper surface Green Group 138B. Lower surface Yellow-Green Group 144A. Size: Average 20-25 mm (l)×8-10 mm (w). Shape: Weak foliaceous appendages on three of the five sepals. Apex: Apiculate. Base: Flat at union with receptacle. Quantity: Five. Surface texture: Upper side: Strongly pubescent. Lower surface: Lightly pubescent. Margins: Pubescent.

Receptacle:

*Surface*.—Smooth.

*Color*.—Yellow-Green Group 144A.

*Shape*.—Urn-shaped.

*Size*.—10 mm (h)×8 mm (w).

Peduncle:

*Surface*.—Smooth.

*Length*.—30 to 40 mm average length.

*Diameter*.—1 to 1.5 mm average diameter.

*Color*.—Yellow-Green Group 144B.

*Strength*.—Moderatley strong.

*Borne*.—Multiple flower buds per stem, generally 2 to 4.

Flower bloom:

*Fragrance*.—None.

*Duration*.—On the plant 4-6 days. As a cut flower, 3-4 days. Senesced petals drop away cleanly.

*Size*.—Small sized for a floribunda rose. When open, the average flower diameter is 60 mm and the average flower height is 30 mm.

*Form*.—Shape of flower when viewed from the side: Upon opening, upper part: Flat. Upon opening, lower part: Flattened convex. Open flower, upper part: Flattened convex. Open flower, lower part: Concave.

Color:

*Upon opening, petals*.—Outermost petals: Outer Side: Basal zone: White Group N155C. Middle zone: Red-Purple Group N74C. Marginal zone: Red-Purple Group 73A. Inner Side: Red-Purple Group N74C. Innermost petals: Outer Side: Red-Purple Group N74B. Inner Side: Purple Group N78A.

*Upon opening, basal petal spots*.—Basal petal spot, outermost petals: Outer Side: White Group 155C. Inner Side: Green-Yellow Group 1D. Basal petal spot, innermost petals: Outer Side: White Group 155C. Inner Side: White Group 155A.

*After opening, petals*.—Outermost petals: Outer Side: Red-Purple Group N74D. Inner Side: Red-Purple Group 73D. Innermost petals: Outer Side: Red-Purple Group N74B and N74C. Inner Side: N74C.

*After opening, basal petal spots*.—Basal petal spot, outermost petals: Outer Side: White Group 155C. Inner Side: White Group 155C. Basal petal spot, innermost petals: Outer Side: White Group 155A. Inner side: White Group 155A.

General tonality: On open flower Purple Group 78D. No change in the general tonality at the end of the 3$^{rd}$ day. Afterwards, general tonality is Purple-Violet Group 80C.

Petals:

*Petal count*.—Double. Average Range: Approximately 35 petals under normal conditions.

*Petal reflex*.—Petals reflex somewhat.

*Petal edge*.—Entire.

*Petal shape*.—Obovate. Apex shape is round. Shape of base is deltoid.

*Petal size*.—25-30 mm (l)×25 mm (w).

*Thickness*.—Average.

*Petal arrangement*.—Not formal.

Petaloids:

*Petaloid count*.—Average of 3-6 per flower.

*Petaloid size*.—Petaloids are 8-10 mm (l)×4-10 mm (w), on average.

*Petaloid color*.—Color of inner side is Red-Purple Group N74C. Color of outer side is Red-Purple Group N74C.

*Petaloid texture*.—Smooth.

*Margins*.—Indented.

*Petaloid shape*.—Most commonly deltoid, with some petaloids very irregular. Apex: Obtuse. Base: Attenuate.

Reproductive organs:

*Pistils*.—Few. Approximately 10-12 present. Stigmas: Location: Slightly inferior in position to anthers. Color: Greyed-Orange Group 163C. Styles: Length: About 4 mm long. Color: Purple Group N79D.

*Stamens*.—Approximately 30 on average and regularly arranged. Anthers: Size: About 1 mm long. Pollen: Present. Color: Greyed-Orange Group 163B. Filaments: Color: Yellow-Green Group 144D. Length: About 8 mm.

THE PLANT

Growth: Vigorous.

Plant habit: Compact and bushy habit. When grown as a budded field grown plant, the average plant height is 70 cm and the average plant width is 50 cm.

Stems:

*Stem color*.—Juvenile stems: Yellow-Green Group 146C. Mature stems: Yellow-Green Group 146A and 146B.

*Stem surface*.—Juvenile stems: Smooth. Mature stems: Smooth.

Prickles: Present.

*Incidence*.—Average of 8-10 per each 10 cm of stem.

*Size*.—Average length: 3-4 mm.

*Color*.—Immature prickles: Yellow-Green Group 146D. Mature prickles: Greyed-Orange Group 174B.

*Anthocyanin*.—Greyed-Red Group 180C on juvenile thorns.

*Shape*.—Concave.

Leaves and leaflets: Normally 5 leaflets on normal leaves in middle of the stem.

*Venation pattern*.—Pyramidal net pattern.

*Leaf size*.—140 mm (l)×80 mm (w).

*Abundance*.—Average.

*Texture*.—Coriaceous. Upper side of leaflet: Semi-glossy and smooth. Under side of leaflet: Matte and smooth.

*Color, mature foliage*.—Upper Leaf Surface: Yellow-Green Group 147A. Lower Leaf Surface: Yellow-Green Group 147B.

*Color, juvenile foliage*.—Upper Leaf Surface: Yellow-Green Group 146A. Lower Leaf Surface: Yellow-Green Group 146B and 146C.

*Anthocyanin intonation*.—Present. Intonations present of Greyed Orange Group 174B on juvenile leaflets and juvenile leaf margins.

Stipules:

*Size*.—25 mm long, 4 mm from distal tip to distal tip.

*Stipule color*.—Yellow-Green Group 146C.

*Margins*.—With stipitate glands.

*Surface*.—Pubescent on upper and lower surfaces.

*Shape*.—Apex: Apiculate. Base: Winged.

Petiole:

*Length*.—Average 20-28 mm.

*Diameter*.—Average 1 mm.

*Petiole color*.—Yellow-Green Group 146C.

*Underneath*.—Finely pubescent with occasional prickle.

*Margins*.—With stipitate glands.

*Anthocyanin*.—Greyed-Orange Group 176B on upper side and margins.

Petiole rachis:

*Length*.—Average 15-20 mm.

*Diameter*.—Average 1 mm.

*Color*.—Yellow-Green Group 146B.

*Underneath*.—Prickles.

*Margins*.—Occasional stipitate glands.

*Anthocyanin*.—Present on upper side and margins of juvenile foliage. Greyed-Orange Group 176B.

Leaflets:

*Size*.—Average size of the terminal leaflet is 50-60 mm (l)×25-30 mm (w).

*Shape*.—Base: Ovate. Apex: Aristate.

*Margins*.—Finely serrated.

*Surface*.—Upper: Semi-glossy. Lower: Matte.

*Texture*.—Coriaceous.

*Arrangement*.—Odd pinnate.

*Venation*.—Pyramidal net pattern.

Hips/seed formation: None observed.

Winter hardiness: To date, the variety has been grown successfully in USDA Zones 5-9.

Disease resistance: Good resistance to Powdery mildew (*Sphaerotheca pannosa*), blackspot (*Diplocarpon rosae*), and rust (*Phragmidium* sp.) diseases under normal growing conditions.

I claim:

1. A new and distinct variety of rose plant, as described and illustrated herein.

* * * * *

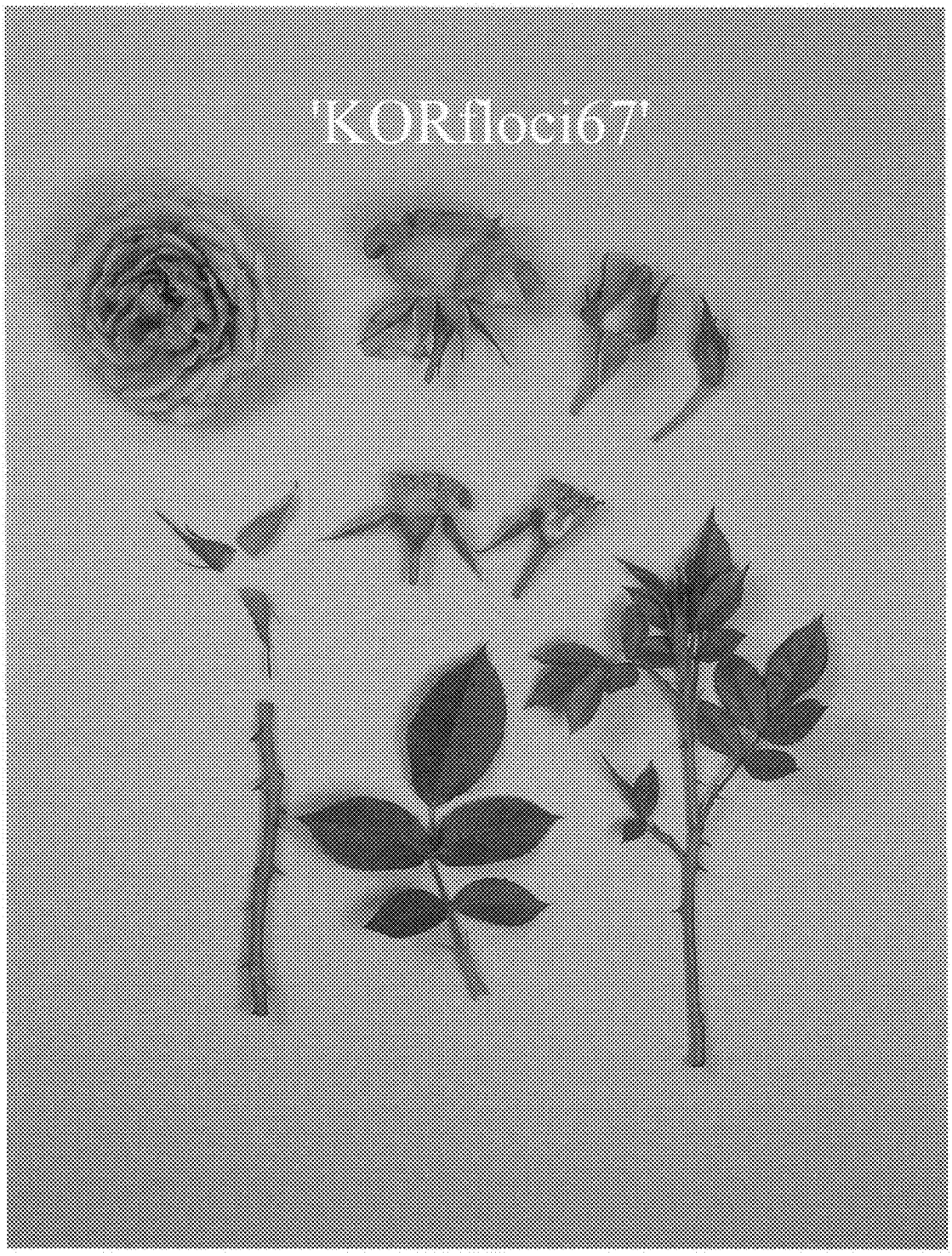
'KORfloc167'